(12) United States Patent
Mizutani

(10) Patent No.: US 6,632,208 B1
(45) Date of Patent: Oct. 14, 2003

(54) SANITARY NAPKIN WITH REINFORCED WINGS

(75) Inventor: Satoshi Mizutani, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/358,584

(22) Filed: Jul. 21, 1999

(30) Foreign Application Priority Data

Jul. 21, 1998 (JP) .......................................... 10-205616

(51) Int. Cl.[7] ................................................. A61F 13/15
(52) U.S. Cl. ............................ 604/385.04; 604/385.31; 604/387
(58) Field of Search ................................. 604/358, 367, 604/378, 385.01, 385.03, 385.04, 385.22, 389, 385.05, 385.31, 387

(56) References Cited

U.S. PATENT DOCUMENTS

| | | | | |
|---|---|---|---|---|
| 5,221,275 A | * | 6/1993 | Van Iten ..................... 604/387 |
| 5,542,941 A | * | 8/1996 | Morita .................. 604/385.04 |
| 5,591,147 A | * | 1/1997 | Couture-Dorschner et al. .. 604/369 |
| 5,649,917 A | * | 7/1997 | Roberts et al. ......... 604/385.01 |
| 5,772,648 A | * | 6/1998 | Osborn, III et al. ..... 604/385.1 |
| 5,851,204 A | * | 12/1998 | Mizutani .................. 604/385.2 |
| 6,277,105 B1 | * | 8/2001 | Rynish ................... 604/385.02 |
| 6,284,943 B1 | * | 9/2001 | Osborn, III et al. ......... 604/366 |
| 6,287,288 B1 | * | 9/2001 | Osborn, III et al. .... 604/385.04 |
| 6,328,722 B1 | * | 12/2001 | Lavash et al. ......... 604/385.04 |

FOREIGN PATENT DOCUMENTS

| | | | |
|---|---|---|---|
| EP | 0 571 981 A1 | 12/1993 | |
| EP | 0 604 764 A1 | 7/1994 | |
| FR | 2 756 728 A3 | 6/1996 | |
| JP | U-7-33314 | 6/1995 | |
| WO | 95/20931 | * 8/1995 | ........... A61F/13/15 |
| WO | WO 97/00655 | 1/1997 | |

OTHER PUBLICATIONS

Copy of European Search Report mailed Feb. 1, 2001.

* cited by examiner

Primary Examiner—Weilun Lo
Assistant Examiner—Jamisue A Webb
(74) Attorney, Agent, or Firm—Butzel Long

(57) ABSTRACT

A sanitary napkin having a napkin body comprising a topsheet, a backsheet and an absorbent core disposed therebetween and a pair of wings at both side edges of the napkin body. The wings comprise a portion of the backsheet extending transversely outward from a middle zone of the side edge of the napkin body and a reinforcing member bonded to an upper surface of the backsheet's portion. Elastically stretchable and contractable cover sheets are bonded to an upper surface of the napkin body.

4 Claims, 3 Drawing Sheets

SANITARY NAPKIN WITH REINFORCED WINGS

BACKGROUND OF THE INVENTION

The present invention relates to a sanitary napkin for personal feminine care, including the absorption of menstrual fluids or similar exudates.

Japanese Utility Model Application Disclosure Gazette (Kokai) No. Hei7-33314 discloses a sanitary napkin provided with wings or flaps, which comprises a napkin body and a pair of wings extending transversely outward from transversely opposite side edges of the napkin body, respectively. The napkin body and the wings are respectively formed on their back sides with adhesive fastening zones for an undergarment worn by a wearer of the sanitary napkin. To wear the sanitary napkin, the adhesive fastening zone formed on the napkin body is anchored on an inner surface of a crotch region of the undergarment and the wings are folded back and fixed to an outer surface of the undergarment.

The wings or flaps of the sanitary napkin are provided with reinforcing sheet strips extending longitudinally of the napkin. The reinforcing sheet strips facilitate the wings to be held and folded.

In the case of the sanitary napkin described in the above-mentioned Japanese Utility Model Application Disclosure Gazette (Kokai) No. Hei7-33314, respective inner side edges of the reinforcing sheet strips rectilinearly extend in parallel to transversely opposite side edges of a liquid-absorbent core of the sanitary napkin. Such arrangement or prior art may often create a feeling of discomfort because the inner side edges of the reinforcing sheet strips are locally pressed against the wearer's legs.

SUMMARY OF THE INVENTION

It is an object of the present invention to provide a sanitary napkin that avoids the creation of a feeling of discomfort.

According to the present invention, there is provided an elongate sanitary napkin having a napkin body which comprises a liquid-pervious topsheet, a liquid-impervious backsheet and a liquid-absorbent core disposed between the topsheet and the backsheet and a pair of wings extending transversely outward from transversely opposite side edges of the napkin body, respectively, which the pair of wings are folded back and fixed to an outer side of a crotch region of an undergarment worn by a wearer of the sanitary napkin, wherein:

each of the wings comprises a portion of the backsheet extending transversely outward from a middle zone of a side edge of the napkin body and a reinforcing sheet strip bonded on an upper surface of the portion of the backsheet, the reinforcing sheet strip having inner and outer side edges both extending in a longitudinal direction of the napkin body wherein the inner side edge is spaced from the side edge of the napkin body and convexly curved toward the outer side edge; a pair of elastically stretchable and contractable cover sheets, each bonded to an upper surface of the napkin body in vicinity of each side edge thereof and extending transversely outward from a substantially full length of the side edge of the napkin body, are bonded to the par of wings, respectively; and the pair of wings are formed on lower surfaces thereof with adhesive fastening zones for the undergarment worn by the wearer of the napkin, respectively.

According to one embodiment of the present invention, each of the cover sheets includes a portion extending transversely inward from each side edge of the napkin body and overlying the topsheet, and the portion overlying the topsheet is bonded under tension in the longitudinal direction to an upper surface of the napkin body at longitudinally opposite ends of the napkin body.

According to another embodiment of the present invention, the cover sheet portion extending transversely outward from each side edge of the napkin body has a region further extending transversely outward beyond the wing and formed on a lower surface thereof with an adhesive fastening zone.

According to still another embodiment of the present invention, the reinforcing sheet strip has a rigidity higher than that of the backsheet as well as that of the cover sheet.

DETAILED DESCRIPTION OF THE PREFERRED EMBODIMENT

Details of a sanitary napkin according to the present invention will be more fully understood from the description given hereunder with reference to the accompanying drawings.

Figure 1:
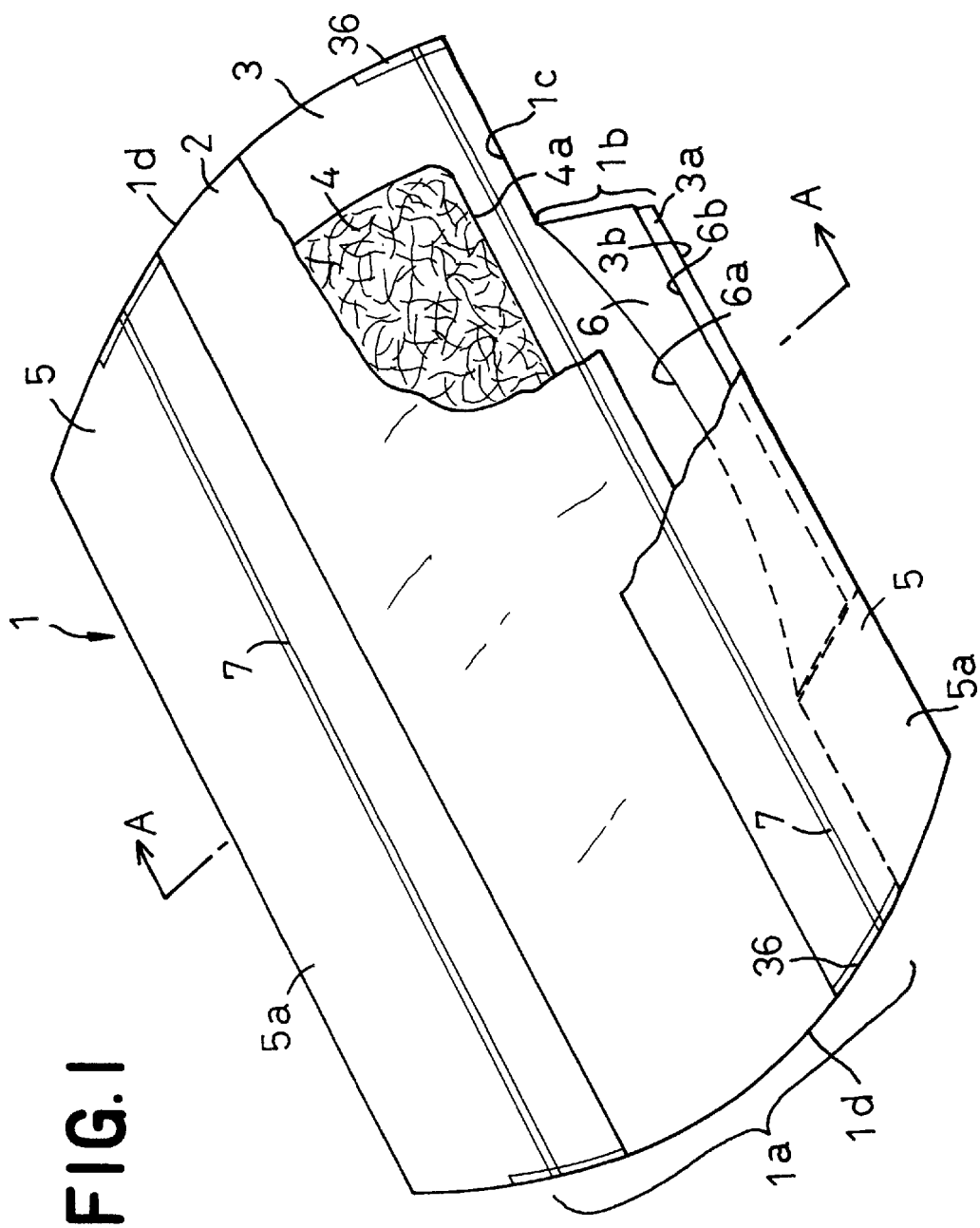
FIG. 1 is a perspective view showing a partially cut away sanitary napkin according to the present invention.
Figure 2:
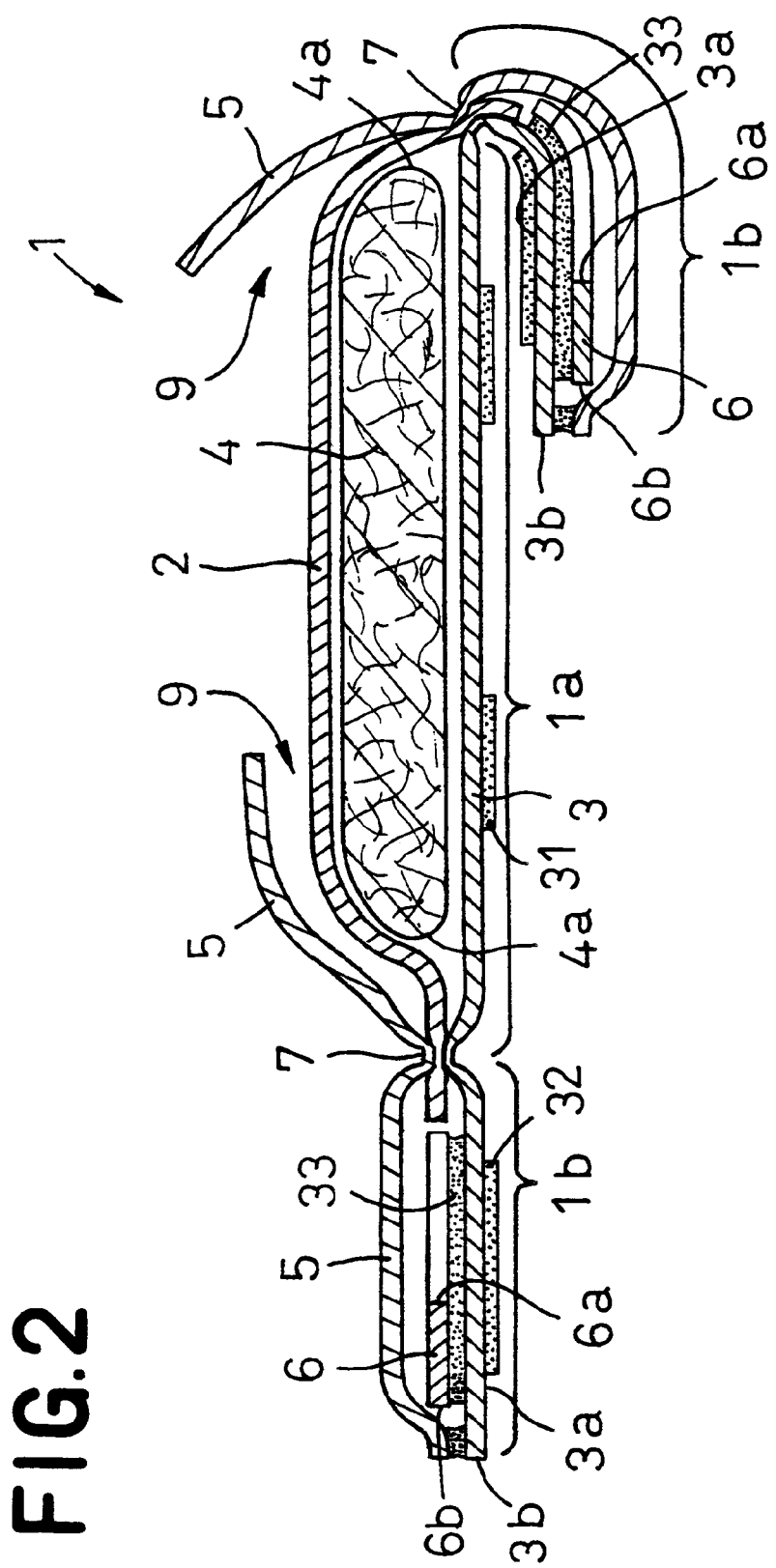
FIG. 2 is a sectional view taken along a line A—A in FIG. 1.

FIG. 1 is a perspective view showing a partially cut away sanitary napkin 1 and FIG. 2 is a sectional view taken along a line A—A in FIG. 1. A sanitary napkin 1 is elongate and comprises a napkin body 1a, a pair of wings 1b extending outward from transversely opposite side edges 1c, respectively, and a pair of cover sheets 5 covering the respective wings 1b.

Referring to FIGS. 1 and 2, the sanitary napkin body 1a comprises a liquid-pervious topsheet 2, a liquid-impervious backsheet 3 and a liquid-absorbent core 4 disposed between these two sheets 2, 3. The liquid-absorbent core 4 is bonded by means of suitable adhesive agent to a lower surface of the topsheet 2 and/or an upper surface of the backsheet 3, depending on the expected effect. The topsheet 2 and the backsheet 3 extend outward beyond longitudinally opposite ends 4a as well as beyond transversely opposite side edges 4a of the absorbent core 4. The topsheet 2 and the backsheet 3 are bonded to each other along these extensions. The backsheet 3 occupying the napkin body 1a is formed on its lower surface with an adhesive fastening zone 31 (See FIG. 2) for an undergarment worn by the wearer.

Each of the wings 1b comprises a backsheet section 3a extending outward from a middle region of the side edge 1c of the napkin body 1a and a reinforcing sheet strip 6 bonded on an upper surface of the backsheet section 3a by means of adhesive agent 33. A lower surface of the wing 1b is applied with suitable adhesive agent to form a fastening zone 32 for the undergarment worn by the wearer.

The reinforcing sheet strip 6 has inner and outer side edges 6a, 6b both extending in the longitudinal direction of the napkin body 1a wherein the inner side edge 6a adjacent the side edge 4a of the absorbent core 4 is convexly curved toward the outer side edge 6b. The reinforcing sheet strip 6 has its longitudinal dimension which is equal to or smaller than that of the backsheet section 3a. The outer side edge 6b of the reinforcing sheet strip 6 may either lie inside or fall in line with the outer side edge 3b of the backsheet section 3a. It is also possible to bond the reinforcing sheet strip 6 to a lower surface of each cover sheet 5.

The reinforcing sheet strip 6 has a rigidity which is higher than that of the backsheet 3 as well as that of the cover sheets 5. The reinforcing sheet strip 6 preferably has a rigidity of 30 mm or higher as measured by a so-called 45 cantilever method according to JIS(Japanese Industry Standard)-L1096. The presence of the reinforcing sheet strip 6 having such high rigidity facilitates the wing 1b to be held and to be folded. Preferable materials for the reinforcing sheet strip 6 include a thin paper, nonwoven fabric, sheet-like pulp and sheet of polyester or polypropylene. It is also possible to apply the wing 1b with adhesive agent such as hot melt adhesive or suitable glue to increase a rigidity of the wing 1b.

Each of the cover sheets 5 is an elastically stretchable and contractable sheet longitudinally extending along each side edge of the napkin body 1a and bonded to the napkin body 1a along a bonding line 7 extending between longitudinally opposite ends 1d. A portion of the cover sheet 5 extending outward beyond the side edge of the napkin body 1a covers the wing 1b and is bonded to the wing 1b. A portion of the cover sheet 5 extending inward from the side edge is bonded under tension in the longitudinal direction of the napkin body 1a to the longitudinally opposite ends 1d of the napkin body 1a along respective bonding line 36. Opposite ends 5a of the cover sheet 5 extending longitudinally of the napkin body 1a beyond the wing 1b may be applied on their lower surfaces with suitable adhesive agent to fasten the ends 5a to a lower surface of the crotch region of the undergarment worn by the wearer, but it should be understood that such an application of adhesive agent is not essential. Between the portion of the cover sheet 5 extending transversely inward and the napkin body 1a, the bonding lines 7, 36 define a pocket 9 adapted to be opened inwardly of the napkin body 1a. It is preferred that the cover sheet 5 can be elastically stretched by about 10~20% in the longitudinal direction of the napkin body 1a as well as in the direction orthogonal to the longitudinal direction.

The elastically stretchable and contractable sheet suitable for use as the cover sheets 5 is an elastic film, elastic nonwoven fabric or the like, preferably having a hydrophobic nature. A laminate of such film and nonwoven fabric may be also useful as the stock material for the cover sheet 5. Such a laminated sheet is preferably used so that the nonwoven fabric comes in contact with the wearer's skin.

Figure 3:
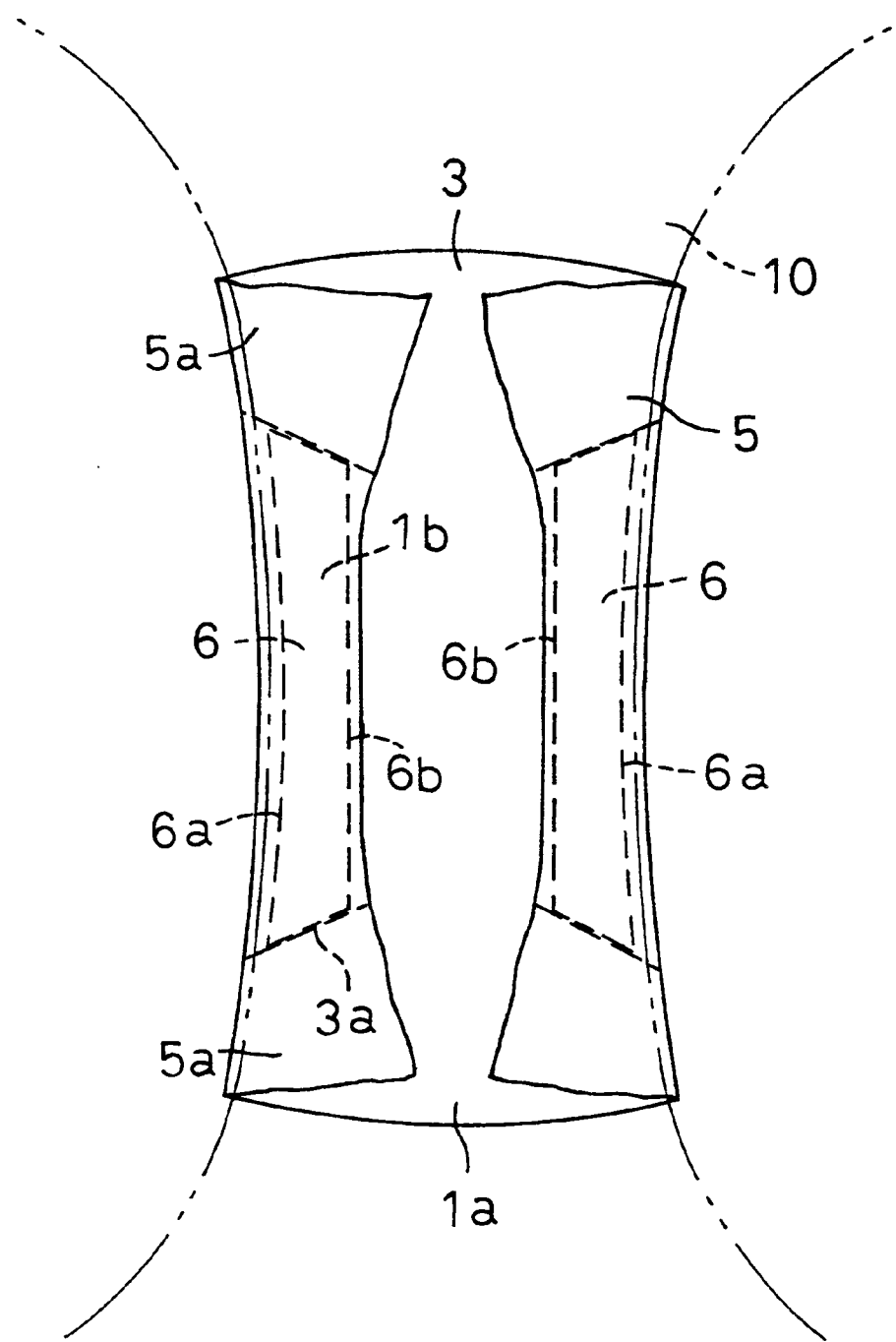
FIG. 3 is a rear view showing the sanitary napkin which is fixed onto an outer side of an undergarment worn by a wearer.

FIG. 3 is a rear view showing the napkin 1 fastened to a crotch region of the undergarment 10 indicated by imaginary lines as the wings 1b have been folded back onto an outer surface of the crotch region. The wings 1b thus folded back are bonded to the outer surface of the undergarment 10 by means of adhesive agent with the respective inner side edges 6a of the reinforcing sheet strips 6 extending along respective peripheries of the leg-openings. In the case of the elastic cover sheets 5 having their lower surfaces made adhesive at their respective longitudinally opposite ends 5a, the ends 5a may be bonded under tension to the outer surface of the undergarment 10 so that the outer surface of the undergarment 10 can be covered with the ends 5 over an extent as large as possible. The sanitary napkin 1 according to the present invention allows the reinforcing sheet strips 6 to be completely covered with the cover sheets 5, preventing the reinforcing sheet strips 6 having a relatively high rigidity from coming in direct contact with and irritating the wearer's skin. When the wings 1b and the reinforcing sheet strips 6 are folded back along the respective peripheries of the leg-openings of the undergarment 10, particularly the cover sheets 5 are preferably pulled in the transverse direction of the napkin 1. Thereby the respective portions of the reinforcing sheet strips 6 extending inwardly are lifted off from an upper surface of the napkin body 1 and the pockets 9 are definitely opened.

With the sanitary napkin according to the present invention, the curved inner side edge of each reinforcing sheet strip extends along each leg-opening's periphery of the undergarment worn by the wearer as each wing is folded back onto the outer surface of the undergarment. Accordingly, there is no apprehension that the reinforcing sheet strip having a relatively high rigidity might be locally pressed against the wearer's leg. The longitudinally opposite ends of each cover sheet covering the wing may be bonded under tension in the transverse direction of the sanitary napkin to the outer surface of the undergarment to ensure that the lower surface of the undergarment's crotch region is covered over as large of an extent as possible. Correspondingly, stain of the undergarment due to body fluids discharged on the sanitary napkin can be minimized. Tensioning of the cover sheets in the transverse direction of the sanitary napkin causes the pockets to be largely opened and thereby facilitates an amount of menstrual discharge tending to flow sideways to be trapped.

What is claimed is:
1. An elongate sanitary napkin comprising:
   a napkin body having opposite side edges and including a liquid-pervious topsheet, a liquid-impervious backsheet and a liquid-absorbent core disposed between said liquid-pervious topsheet and said liquid-impervious backsheet;
   a pair of wings extending transversely outward from transversely opposite side edges of said napkin body, so that said pair of wings can be folded back and bonded to an outer surface of a crotch region of an undergarment worn by a wearer of said sanitary napkin, each of said wings including:
      a portion of said liquid-impervious backsheet which extends transversely outward from a middle zone of a side edge of said napkin body; and
      a reinforcing sheet strip bonded on an upper surface of the portion of said liquid-impervious backsheet along a side edge of said liquid-impervious backsheet, said reinforcing sheet strip having inner and outer edges extending in the longitudinal direction of said napkin body, said inner side edge of said reinforcing sheet strip being spaced outwardly from said side edge of said napkin body and convexly curved toward said outer side edge of said reinforcing sheet when said wings are positioned so as to extend laterally outward from sides of said napkin body;

a pair of elastically stretchable and contractible cover sheets, each bonded to an upper surface of said napkin body adjacent each side edge of said napkin body and extending transversely outward from a substantially entire zone of said side edge of said napkin bode, each of said elastically stretchable and contractible cover sheets being bonded to one of said pair of wings; and adhesive fastening zones formed on lower surfaces of said pair of wings.

2. A sanitary napkin according to claim 1, wherein each of said cover sheets includes a portion which extends transversely inward from each side edge of said napkin body and overlies said liquid-pervious topsheet, said portion overlying said liquid-pervious topsheet being bonded under tension in said longitudinal direction to the upper surface of said napkin body at longitudinally opposed ends of said napkin body.

3. A sanitary napkin according to claim 1, wherein regions of said cover sheets which extend longitudinally beyond said pair of wings are formed on lower surfaces thereof with adhesive fastening zones.

4. A sanitary napkin according to claim 1, wherein said reinforcing sheet strip has a higher rigidity than a rigidity of either said liquid-impervious backsheet or said cover sheet.

\* \* \* \* \*